United States Patent
Copes

(10) Patent No.: US 6,420,631 B1
(45) Date of Patent: Jul. 16, 2002

(54) INBRED CANTALOUPE GDM3

(75) Inventor: Wilson B. Copes, Sacramento, CA (US)

(73) Assignee: Harris Moran Seed Company, Modesto, CA (US)

( * ) Notice: Subject to any disclaimer, the term of this patent is extended or adjusted under 35 U.S.C. 154(b) by 0 days.

(21) Appl. No.: 09/571,319

(22) Filed: May 15, 2000

(51) Int. Cl.$^7$ ............... A01H 1/00; A01H 5/00; A01H 5/10; C12N 5/04

(52) U.S. Cl. ............ 800/309; 800/260; 800/278; 435/420

(58) Field of Search ............... 800/200, 205, 800/265, 266, 267, 274, 278, 300, 301, 302, 309, 260, 420; 435/421, 430, 430.1

(56) References Cited

U.S. PATENT DOCUMENTS 5,777,196 A * 7/1998 Hall ..................... 800/200
5,948,957 A * 9/1999 Chapko et al. ......... 800/320.1
5,969,212 A * 10/1999 Getschman ............. 800/200

OTHER PUBLICATIONS

Adelberg, JW, et al. 1994. Explant origin affects the frequency of tetraploid plants from tissue culture of melon. HortScience 29(6);689–692.*

Ezura, H, et al. 1994 Ploidy of somatic embryos and the ability to regenerate plantlets in melons (*Cucumis melo* L.) Plant Cell Reorts 14: 107–111.*

Ezura, H., et al. 1995. Selection of somaclonal variants with low–temperature germinability in melon (*Cucumis melo* L.) Plant Cell Reports 14:684–688.*

Zink, FW, et al. 1987. U.C. Top Mark Fusarium Wilt–resistant (Fom–1) Muskmelon Breeding line. HortScience 22(6):1342.*

Zhang et al. 1996. Development of genic male–sterile watermelon lines with delayed–green seedling marker. HortScience 31(1):123–126.*

Bennetzen, J.L. et al. 1992. Approaches and progress in the molecular cloning of plnt disease resistance genes. Genetic Engineering 14: 99–124.*

De Bolle M.F.C. et al. 1996 Antimicrobal peptides form *Mirabilis jalapa* and *Amaranthus cudatus*: expression, processing, localization and biological activity in transgenic tobacco. Plant Molec. Biol. 31: 993–1008.*

Pang, S–H et al. 1992. Expression of a gene encoding a scorpion insectotoxin peptide in yeast bacteria and plants. Gene 116:165–172.*

* cited by examiner

Primary Examiner—David T. Fox
Assistant Examiner—Francis P. Moonan
(74) Attorney, Agent, or Firm—Rothwell, Figg, Ernst & Manbeck

(57) ABSTRACT

An inbred cantaloupe line, designated GdM3, is disclosed. The invention relates to the seeds of inbred cantaloupe line GdM3, to the plants of inbred cantaloupe line GdM3 and to methods for producing a cantaloupe plant produced by crossing the inbred line GdM3 with itself or another cantaloupe line. The invention further relates to hybrid cantaloupe seeds and plants produced by crossing the inbred line GdM3 with another cantaloupe line.

25 Claims, No Drawings

INBRED CANTALOUPE GDM3

BACKGROUND OF THE INVENTION

The present invention relates to a new and distinctive cantaloupe inbred line, designated GdM3. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, fruit quality, resistance to diseases and insects, better stalks and roots, tolerance to drought and heat, and better agronomic quality.

Practically speaking, all cultivated forms of cantaloupe belong to the highly polymorphic species *Cucumis melo* L. that is grown for its sweet edible fruit. The term cantaloupe, as used herein, refers to the American usage of the term which is used to describe the netted melons commonly referred to as cantaloupe or muskmelon in U.S. commerce. As a crop, cantaloupes are grown commercially wherever environmental conditions permit the production of an economically viable yield. They are produced on non-climbing vines that are prostrate on the soil. On healthy plants there is a canopy of large, soft, hairy leaves, generally heart shaped and somewhat lobed. Fruits may be orange fleshed or green fleshed. The fruit surface is generally netted and roughened and in some varieties sutured. Fruit shape is generally round to oval and ranges in size from five to eight inches long and about equal in diameter. In the United States, the principal fresh market cantaloupe growing regions are California, Arizona and Texas which produce approximately 96,000 acres out of a total annual acreage of more than 113,000 acres (USDA, 1998). Fresh cantaloupes are available in the United States year-round although the greatest supply is from June through October. Fresh cantaloupes are consumed in many forms. They are eaten sliced or diced and used as an ingredient in many prepared foods.

*Cucumis melo* is a member of the family Cucurbitaceae. The Cucurbitaceae is a family of about 90 genera and 700 to 760 species, mostly of the tropics. The family includes pumpkins, squashes, gourds, watermelon, loofah and several weeds. The genus Cucumis, to which the cantaloupe, cucumbers, and several melons belong, includes about 70 species. *Cucumis melo* includes a wide range of cultivated plants. Although crosses outside the species are sterile, intraspecific crosses are generally fertile, resulting in a confusing range of variation. The more common cultivated plants fall into four main groups. First are the true cantaloupes of Europe. These have thick, scaly, rough, often deeply grooved, but not netted rinds. Second are the muskmelons, mostly grown in the United States, where they are incorrectly called cantaloupes. These have finely netted rinds with shallow ribs. Third are the casaba or winter melons with large fruits. These have smooth, often yellow rinds. The honeydew melons are in this third group. Fourth are a group of elongated melons of India, China and Japan which are grown as vegetables. Other classification schemes and peculiar cultivars could be presented.

Cantaloupe is a simple diploid species with twelve pairs of highly differentiated chromosomes. Large field spaces are required for cantaloupe and the need for labor intensive hand pollination for selfing as well as cross pollination has resulted in a lag in the knowledge of cantaloupe genetics relative to such crops as tomato. Cantaloupe flowers open after sunrise; the exact time depends on environmental conditions such as sunlight, temperature and humidity. The flower closes permanently in the afternoon of the same day. Almost all pollen is collected and transferred before noon. Typically flowers are staminate although some are also hermaphroditic. Although hermaphroditic flowers are self-fertile, they are incapable of performing self-pollination. Insects are required for pollination. The primary pollinators are bees, particularly honey bees.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior cantaloupe inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same cantaloupe traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new cantaloupe inbred line.

The development of commercial cantaloupe hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of hetero-zygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Cantaloupe is an important and valuable crop. Thus, a continuing goal of plant breeders is to develop stable, high yielding cantaloupe hybrids that are agronomically sound. The reasons for this goal are obviously to maximize the amount of melon fruits produced on the land used. To accomplish this goal, the cantaloupe breeder must select and develop cantaloupe plants that have the traits that result in superior parental lines for producing hybrids.

SUMMARY OF THE INVENTION

According to the invention, there is provided a novel inbred cantaloupe line, designated GdM3. This invention thus relates to the seeds of inbred cantaloupe line GdM3, to the plants of inbred cantaloupe line GdM3 and to methods for producing a cantaloupe plant produced by crossing the inbred line GdM3 with itself or another cantaloupe line. This invention further relates to hybrid cantaloupe seeds and plants produced by crossing the inbred line GdM3 with another cantaloupe line.

The inbred cantaloupe plant of the present invention may further comprise, or have, a cytoplasmic factor that is capable of conferring male sterility. Parts of the cantaloupe plant of the present invention are also provided, such as e.g., pollen obtained from an inbred plant and an ovule of the inbred plant.

In one aspect, the present invention provides for single gene converted plants of GdM3. The single transferred gene may preferably be a dominant or recessive allele. Preferably, the single transferred gene will confer such traits as male sterility, herbicide resistance, insect resistance, resistance for bacterial, fungal, or viral disease, male fertility and enhanced nutritional quality. The single gene may be a naturally occurring cantaloupe gene or a transgene introduced through genetic engineering techniques.

In another aspect, the present invention provides regenerable cells for use in tissue culture or inbred cantaloupe plant GdM3. The tissue culture will preferably be capable of regenerating plants having the physiological and morphological characteristics of the foregoing inbred cantaloupe plant, and of regenerating plants having substantially the same genotype as the foregoing inbred cantaloupe plant. Preferably, the regenerable cells in such tissue cultures will be embryos, protoplasts, meristematic cells, callus, pollen, leaves, anthers, roots, root tips, or flowers. Still further, the present invention provides cantaloupe plants regenerated from the tissue cultures of the invention.

Definitions

In the description and tables which follow, a number of terms are used. In order to provide a clear and consistent understanding of the specification and claims, including the scope to be given such terms, the following definitions are provided:

Allele. The allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Cavity. As used herein, cavity refers to the center of the cantaloupe fruit containing seeds and maternal tissues.

Essentially all the physiological and morphological characteristics. A plant having essentially all the physiological and morphological characteristics means a plant having the physiological and morphological characteristics, except for the characteristics derived from the converted gene.

Number of Boxes per Acre. As used in Table 3 and 4, the Number of Boxes per Acre—6's, 9's, 12's, 15's, 18's or 23's refers to the number of fruit that fit into a standard cantaloupe box.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Soluble Solids. Soluble solids refers to the percent of solid material found in the fruit tissue, the vast majority of which is sugars.

DETAILED DESCRIPTION OF THE INVENTION

Inbred cantaloupe line GdM3 has superior characteristics, and provides an excellent parental line in crosses for producing first generation ($F_1$) hybrid cantaloupe.

During the development of GdM3, the single cross of Gd×M3 was made. After this initial cross was made, the pedigree selection method was then used for inbred advancement, alternating between field selections in both Davis, Calif. and Florida and selecting for horticultural traits and monoeciousness and also greenhouse selections for disease resistance genes. Selection pressure was for monoeciousness, early maturity, high soluble solids, bright orange internal color, large fruit size, strong net, firm flesh, normal abscission profile, slight oval shape as well as tolerance to fusarium wilt race 2 and one or more races of powdery mildew.

Inbred cantaloupe line GdM3 has the following morphologic and other characteristics (based primarily on data collected at Davis, Calif.).

Variety Description Information

1. TYPE: Monoecious
2. REGION WHERE DEVELOPED: California, Arizona and Florida
3. MATURITY: 75 days
4. FRUIT:
   Orange fleshed with green rind
   Completely Netted
5. SIZE:
   Diameter—14.35 cm
   Length—15.23 cm
   Cavity—6.66 cm
   Cavity/Diameter Ratio—0.46%
   Soluble Solids—13.46
6. DISEASE RESISTANCE
   Resistant *Fusarium Oxysporum* f.sp. melonis, race 0, 2
   Tolerant *Sphaerotheca fuliginea* U.S. designated race 1, 2

This invention is also directed to methods for producing a cantaloupe plant by crossing a first parent cantaloupe plant with a second parent cantaloupe plant, wherein the first or second cantaloupe plant is the inbred cantaloupe plant from the line GdM3. Further, both first and second parent cantaloupe plants may be from the inbred line GdM3. Therefore, any methods using the inbred cantaloupe line GdM3 are part of this invention: selfing, backcrosses, hybrid breeding, and crosses to populations. Any plants produced using inbred cantaloupe line GdM3 as a parent are within the scope of this invention. Advantageously, the inbred cantaloupe line is used in crosses with other cantaloupe varieties to produce first generation ($F_1$) cantaloupe hybrid seed and plants with superior characteristics.

As used herein, the term "plant" includes plant cells, plant protoplasts, plant cell of tissue culture from which cantaloupe plants can be regenerated, plant calli, plant clumps, and plant cells that are intact in plants or parts of plants, such as pollen, flowers, leaves, stalks, and the like.

The present invention contemplates a cantaloupe plant regenerated from a tissue culture of an inbred (e.g., GdM3) or hybrid plant of the present invention. As is well known in the art, tissue culture of cantaloupe can be used for the in vitro regeneration of a cantaloupe plant.

Thus, another aspect of this invention is to provide for cells which upon growth and differentiation produce the inbred line GdM3.

GdM3 is similar to the public cultivar 'Topmark'. Topmark is also a full netted western shipping type cantaloupe. While similar to GdM3, Topmark has numerous differences including: GdM3 matures at least 4 days earlier than Topmark. GdM3 is oval in shape while Topmark is round. GdM3 has the monoecious sex characteristic while Topmark is andromonoecious. GdM3 is resistant to Fusarium wilt race 2 and one or more races of powdery mildew while Topmark is susceptible. The fruits of GdM3 are approximately 15% larger than the fruits of Topmark.

Some of the criteria used to select fruits/plants in various generations include: monoeciousness, early maturity, high soluble solids, bright orange internal color, large fruit size, strong net, firm flesh, normal abscission profile, slight oval shape as well as tolerance to Fusarium wilt race 2 and one or more races of powdery mildew. During the development of the line, crosses were made to inbred testers for the purpose of estimating the line's general and specific combining ability, and evaluations were run by the Davis, Calif. Research Station. The inbred was evaluated further as a line and in numerous crosses by other research stations across the United States. The inbred has proven to have a very good combining ability in hybrid combinations.

The inbred has shown uniformity and stability. It has been self-pollinated a sufficient number of generations, with careful attention to uniformity of plant type to ensure homozygosity and phenotypic stability. The line has been increased both by hand and sibbed in isolated fields with continued observations for uniformity. No variant traits have been observed or are expected in GdM3.

Tables

As shown in Tables 1 and 2, phenotypic variation for important fruit characteristics is minimal and falls within the normal distribution for a uniform line considering the genetic by environment component. Additionally, comparing means of Table 1 and Table 2 indicates phenotypic stability between two different locations of line GdM3.

TABLE 1

Yuma, Arizona
June, 1999

| Wt. (kg) | Soluble Solids | Fruit Diameter (cm) | Fruit Length (cm) | Cavity (cm) | Cav/Diam Ratio |
|---|---|---|---|---|---|
| Location 1 - Plot 99YU5410 | | | | | |
| 1.26 | 14.8 | 5.25 | 5.5 | 2.63 | 0.50 |
| 1.52 | 13.7 | 5.75 | 5.5 | 2.75 | 0.48 |
| 1.43 | 13.2 | 5.75 | 5.5 | 2.75 | 0.48 |
| 1.73 | 15.2 | 5.75 | 6.25 | 2.88 | 0.50 |
| 1.41 | 13.0 | 5.5 | 6.0 | 2.5 | 0.45 |
| 1.9 | 13.4 | 6.0 | 6.25 | 2.5 | 0.42 |
| 2.11 | 13.6 | 6.13 | 7.0 | 2.75 | 0.45 |
| 1.37 | 11.4 | 5.38 | 6.0 | 2.25 | 0.42 |
| 2.08 | 13.0 | 6.25 | 6.38 | 3.0 | 0.48 |
| 1.92 | 14.2 | 5.75 | 6.5 | 2.63 | 0.46 |
| 1.67 | 13.55 | 5.75 | 6.09 | 2.66 | 0.46 |

TABLE 2

Yuma, Arizona
June, 1999

| Wt. (kg) | Soluble Solids | Fruit Diameter (cm) | Fruit Length (cm) | Cavity (cm) | Cav/Diam Ratio |
|---|---|---|---|---|---|
| Location 2 - Plot 99YU5411 | | | | | |
| 1.78 | 15.0 | 6.0 | 5.5 | 2.63 | 0.44 |
| 1.51 | 14.8 | 5.5 | 5.5 | 2.75 | 0.50 |
| 1.84 | 14.2 | 5.75 | 5.5 | 2.75 | 0.48 |
| 1.55 | 13.4 | 5.38 | 6.25 | 2.88 | 0.54 |
| 1.83 | 13.2 | 5.75 | 6.0 | 2.5 | 0.43 |
| 1.26 | 12.0 | 5.25 | 6.25 | 2.5 | 0.48 |
| 1.64 | 13.2 | 5.75 | 7.0 | 2.75 | 0.48 |
| 1.96 | 12.2 | 5.88 | 6.0 | 2.25 | 0.38 |
| 1.47 | 11.4 | 6.25 | 6.38 | 3.0 | 0.48 |
| 1.81 | 14.2 | 5.75 | 6.5 | 2.63 | 0.46 |
| 1.67 | 13.36 | 5.73 | 6.09 | 2.66 | 0.46 |

TABLE 2-continued

Yuma, Arizona
June, 1999

| Wt. (kg) | Soluble Solids | Fruit Diameter (cm) | Fruit Length (cm) | Cavity (cm) | Cav/Diam Ratio |
|---|---|---|---|---|---|

As shown in Tables 3 and 4, HMX 7605 (with female parent line GdM3) shows a unique size distribution profile when compared to it's closest early season competitors Primo and Impac.

TABLE 3

Cantaloupe Variety Trial-Early Season
Carl Schuster Farms-Plant Date: January 25, 1999

| Variety | Number of Boxes per Acre | | | | | | Total # Boxes |
|---|---|---|---|---|---|---|---|
| | 6's | 9's | 12's | 15's | 18's | 23's | |
| HMX-7605 | 198.05 | 87.12 | 89.85 | 320.20 | 101.69 | 21.30 | 816.21 |
| Primo | 70.79 | 50.82 | 87.14 | 411.64 | 105.31 | 14.20 | 739.90 |
| Impac | 484.65 | 112.53 | 111.64 | 198.01 | 39.94 | 1.42 | 948.19 |

TABLE 4

Cantaloupe Variety Trial-Early Season
Ringgold Farms-Plant Date: January 27, 1999

| Variety | Number of Boxes per Acre | | | | | | Total # Boxes |
|---|---|---|---|---|---|---|---|
| | 6's | 9's | 12's | 15's | 18's | 23's | |
| HMX-7605 | 98.04 | 76.23 | 78.96 | 209.08 | 88.98 | 17.04 | 568.33 |
| Primo | 0.00 | 43.56 | 59.89 | 270.07 | 98.04 | 28.98 | 498.54 |
| Impac | 353.96 | 225.06 | 117.08 | 178.60 | 30.88 | 1.42 | 907.00 |

As shown in Table 5, the mean percent of soluble solids for several early season cantaloupe cultivars at 3 locations are given. The mean figures within a column followed by the same letter are not significantly different, (p=0.05, Duncans' Multiple Range Test).

TABLE 5

Percent soluble solids for early-season cantaloupe cultivars

| Cultivar | Schuster | E&S | Suntex |
|---|---|---|---|
| Trooper | 12.6 a | 11.3 a | 12.0 a |
| Primo | 11.9 ab | 11.5 a | 10.6 b |
| HMX7605 | 11.4 b | 10.1 b | 9.3 bc |
| HMX6583 | 11.2 bc | 9.6 bc | 10.1 b |
| RML7908-VP | 11.1 bc | 9.4 bc | 7.7 d |
| HMX6584 | 11.1 bc | 10.3 b | 9.5 bc |
| ValleyPac | 11.0 bc | 9.5 bc | — |
| AChaparral | 10.8 bc | 10.2 b | 10.1 b |
| Early Delight | 10.8 bc | 10.1 b | 9.4 bc |
| Impac | 10.2 c | 8.7 c | 9.9 b |
| SME7123 | — | — | 8.4 cd |

When the term inbred cantaloupe plant is used in the context of the present invention, this also includes any single gene conversions of that inbred. The term single gene converted plant as used herein refers to those cantaloupe plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental cantaloupe plants for that inbred. The parental cantaloupe plant which contributes the gene for the desired characteristic is termed the nonrecurrent or donor parent. This terminology refers to the fact that the nonrecurrent parent is used one time in the backcross protocol and therefore does not recur. The parental cantaloupe plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a cantaloupe plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

A further aspect of the invention relates to tissue culture of cantaloupe plants designated GdM3. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, leaves, roots, root tips, and the like. In a preferred embodiment, tissue culture is embryos, protoplast, meristematic cells, pollen, leaves or anthers. Means for preparing and maintaining plant tissue culture are well known in the art. By way of example, a tissue culture comprising organs has been used to produce regenerated plants as described in Dirks R., et al. (1989) In vitro plant regeneration from leaf and cotyledon explants in *Cucumis melo*. PI Cell Rep 7:626–627; Tahar, S. B., et al. (1989) Regeneration and Transformation of Muskmelon. Cucurb Genet Coop 12:21–27; Homma, Y., et al. (1991) Improvement in Production and Regeneration of Somatic Embryos from Mature Seed of Melon (*Cucumis-Melo* L) on Solid Media. Japan J Breed 41:543–551 (Y Homma Shizuoka Agr Expt Stn Shizuoka 438, Japan); Yoshioka, K., et al. (1992) Successful Transfer of the Cucumber Mosaic Virus Coat Protein Gene to *Cucumis melo* L. Japan J Breed 42:277–285; Debeaujon, I., et al. (1992) Induction of Somatic Embryogenesis and Caulogenesis from Cotyledon and Leaf Protoplast-Derived Colonies of Melon (*Cucumis Melo* L.). PI Cell Rep 12:37–40; Tabei, Y., et al. (1992) Shoot Regeneration from Cotyledonary Protoplasts of Melon (*Cucumis melo* L. cv. *Charentais*). J Jap Soc Hort Sci 61:317–322; Debeaujon, I., et al. (1993) Somatic Embryogenesis in Cucurbitaceae. Plant Cell Tissue Org Cult 34:91–100; Fang, G. W., et al. (1993) Genetic Engineering of Potyvirus Resistance Using Constructs Derived from the Zucchini Yellow Mosaic Virus Coat Protein Gene. Molecular Plant—Microbe Interactions 6:358–367; Valles, M. P., et al. (1994) Agrobacterium-Mediated Transformation of Commercial Melon (*Cucumis melo* L, cv *Amarillo Oro*). PI Cell Rep 13:145–148; Ezura, H., et al. (1994) Ploidy of somatic embryos and the ability to regenerate plantlets in melon (*Cucumis melo* L). PI Cell Rep 14:107–111; Ezura, H., et al. (1995) Selection of somaclonal variants with low-temperature germinability in melon (*Cucumis melo* L.). PI Cell Rep 14:684–688; Kathal, R., et al. (1994) Plant Regeneration from the Callus Derived from Root Explants of *Cucumis Melo* L CV *Pusa Sharbati*. Plant Sci 96:137–142; Adelberg, J. W., et al. (1994) Explant Origin Affects the Frequency of Tetraploid Plants from Tissue Cultures of Melon. Hortscience 29:689–692.

DEPOSIT INFORMATION

A deposit of the inbred cantaloupe GdM3 seed of this invention is maintained by Harris Moran Seed Company, 9241 Mace Boulevard, Davis, Calif. 95616. Access to this deposit will be available during the pendency of this application to persons determined by the Commissioner of Patents and Trademarks to be entitled thereto under 37 CFR 1.14 and 35 USC 122. Upon allowance of any claims in this application, all restrictions on the availability to the public of the variety will be irrevocably removed by affording access to a deposit of at least 2,500 seeds of the same variety with the American Type Culture Collection, Manassas, Va.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred cantaloupe seed designated GdM3, a sample of said seed having been deposited under ATCC Accession No. PTA-4193.

2. A cantaloupe plant, or parts thereof, produced by growing the seed of claim 1.

3. Pollen of the plant of claim 2.

4. An ovule of the plant of claim 2.

5. A cantaloupe plant, or parts thereof, having all of the physiological and morphological characteristics of the cantaloupe plant of claim 2.

6. A tissue culture of cells of a cantaloupe plant of the inbred line GdM3, the cells being from a tissue selected from the group consisting of leaves, pollen, embryos, roots, flowers, an stalks.

7. A method for producing a hybrid cantaloupe seed comprising crossing a first inbred parent cantaloupe plant with a second inbred parent cantaloupe plant and harvesting the resultant hybrid cantaloupe seed, wherein said first or second parent cantaloupe plant is the cantaloupe plant of claim 2.

8. A hybrid cantaloupe seed produced by the method of claim 7.

9. A hybrid cantaloupe plant, or parts thereof, produced by growing said hybrid cantaloupe seed of claim 8.

10. Cantaloupe seed produced by growing said hybrid cantaloupe plant of claim 9.

11. A cantaloupe plant, or parts thereof, produced from seed of claim 10.

12. A method for producing a hybrid cantaloupe seed comprising crossing an inbred plant according to claim 2 with another, different cantaloupe plant.

13. A hybrid cantaloupe seed produced by the method of claim 12.

14. A hybrid cantaloupe plant, or its parts, produced by growing said hybrid cantaloupe seed of claim 13.

15. Cantaloupe seed produced from said hybrid cantaloupe plant of claim 14.

16. A cantaloupe plant, or its parts, produced from the cantaloupe seed of claim 15.

17. A method for producing a GdM3-derived cantaloupe plant, comprising:
  a) crossing inbred cantaloupe line GdM3, a sample of seed of said line having been deposited under ATCC accession number , with a second cantaloupe plant to yield progeny cantaloupe seed;
  b) growing said progeny cantaloupe seed, under plant growth conditions, to yield said GdM3-derived cantaloupe plant.

18. The method of claim 17, further comprising:
  c) crossing said GdM3-derived cantaloupe plant with itself or another cantaloupe plant to yield additional GdM3-derived progeny cantaloupe seed;
  d) growing said progeny cantaloupe seed of step (c) under plant growth conditions, to yield additional GdM3-derived cantaloupe plants;
  e) repeating the crossing and growing steps of (c) and (d) from 0 to 7 times to generate further GdM3-derived cantaloupe plants.

19. The method of claim 17, still further comprising utilizing plant tissue culture methods to derive progeny of said GdM3-derived cantaloupe plant.

20. The cantaloupe plant, or parts thereof, of claim 2, wherein the plant or parts thereof have been transformed so that its genetic material contains one or more transgenes operably linked to one or more regulatory elements.

21. A method for producing a cantaloupe plant that contains in its genetic material one or more transgenes, comprising crossing the cantaloupe plant of claim 20 with either a second plant of another cantaloupe line, or a non-transformed cantaloupe plant of the line GdM3, so that the genetic material of the progeny that result from the cross contains the transgene(s) operably linked to a regulatory element.

22. Cantaloupe plants, or parts thereof, produced by the method of claim 21.

23. A method for developing a cantaloupe plant in a cantaloupe plant breeding program using plant breeding techniques which include employing a cantaloupe plant, or its parts, as a source of plant breeding material comprising: using the cantaloupe plant, or its parts, of claim 2 as a source of said breeding material.

24. The cantaloupe plant of claim 5, further comprising a single gene conversion.

25. The single gene conversion cantaloupe plant of claim 24, wherein the gene is selected from the group consisting of: a transgene, a dominant allele, and a recessive allele.

* * * * *